(12) United States Patent
Montner

(10) Patent No.: US 6,221,910 B1
(45) Date of Patent: Apr. 24, 2001

(54) GLUTAMINE CONTAINING ORAL REPLACEMENT SOLUTION

(75) Inventor: Paul Montner, Albuquerque, NM (US)

(73) Assignee: The University of New Mexico, Albuquerque, NM (US)

( * ) Notice: Subject to any disclaimer, the term of this patent is extended or adjusted under 35 U.S.C. 154(b) by 0 days.

(21) Appl. No.: 09/358,462

(22) Filed: Jul. 22, 1999

(51) Int. Cl.⁷ .................................................. A61K 31/195
(52) U.S. Cl. ............................................. 514/563; 514/58
(58) Field of Search ....................... 514/563, 58

(56) References Cited

U.S. PATENT DOCUMENTS

| | | |
|---|---|---|
| 3,717,470 | 2/1973 | Yokotsuka et al. . |
| 4,479,974 | 10/1984 | Schenz . |
| 5,171,597 | 12/1992 | Erfan . |
| 5,183,674 | 2/1993 | Olin . |
| 5,270,297 | 12/1993 | Paul et al. . |
| 5,292,722 * | 3/1994 | Wilmore ................................ 514/23 |
| 5,411,757 | 5/1995 | Buist et al. . |
| 5,420,107 | 5/1995 | Brooks . |
| 5,438,043 | 8/1995 | Ljungqvist . |
| 5,561,111 * | 10/1996 | Guerrant et al. ....................... 514/17 |
| 5,624,907 | 4/1997 | Ljungqvist . |
| 5,817,364 | 10/1998 | Olin . |
| 5,962,733 * | 10/1999 | Lall et al. ............................. 562/563 |
| 6,051,236 * | 4/2000 | Portman ............................. 424/195.1 |

* cited by examiner

Primary Examiner—James H. Reamer
(74) Attorney, Agent, or Firm—Hoffman, Wasson & Gitler

(57) ABSTRACT

The invention focuses on a glutamine containing oral replacement solution for endurance exercise and rehydration. The solution uniquely combines the specific amino acid glutamine with a carbohydrate such as maltodextrin and sodium to enhance absorption of the other components and replace glutamine depletion in worked muscles as well as other areas of the body.

7 Claims, No Drawings

GLUTAMINE CONTAINING ORAL REPLACEMENT SOLUTION

BACKGROUND OF THE INVENTION

The invention generally relates to a beverage, or the like, for all forms of endurance exercise, work and recreational activities requiring or benefitting from fluid replacement during the activity. In addition, the beverage and its unique formulation can be used for rehydration after the activity or exercise is completed. More particularly, the invention is directed to the use of the specific amino acid, glutamine, as an essential component for a sports beverage.

Oral replacement solutions have been well demonstrated to enhance endurance performance by providing water to maintain hydration status, electrolytes (primarily sodium) to avoid disturbances such as hyponatremia, and carbohydrates to provide energy and prevent glycogen depletion. For oral replacement solution components to be utilized by the body, these components must be emptied from the stomach and absorbed in the intestines. Gastric emptying has been shown to be affected by volume and temperature of the fluid ingested as well as the osmolality and caloric density. Studies have shown that gastric emptying and intestinal absorption are limited to approximately two liters per hour. Of particular interest are substances, through passive or active transport through the intestinal lining, that can increase the absorption of water.

It has been well demonstrated that the addition of sugars to solutions will further enhance sodium and water absorption to an active transport mechanism. For example, a molecule of glucose, when absorbed, will transport two sodium ions with it, resulting in additional absorption of water. Other sugars such as fructose also have transport mechanisms for sodium that are independent of glucose. Thus, enhanced intestinal absorption of water is achieved with a carbohydrate-electrolyte mix and these are standard components or oral replacement solutions. However, these standard mixes do not achieve optimal absorption of water.

In addition, glutamine offers other benefits, including improved immunity and resistance to infection, maintenance of intestinal tract integrity, and restoration of muscle mass. There is no prior art disclosing these benefits or our specific beverage composition.

One particular energy supply composition was disclosed in U.S. Pat. No. 5,817,364. This patent focused on a beverage containing alpha-ketoglutaric acid. This patent specifically describes an energy supply composition, beverage or dry, suitable for use during, or after physical exertion which requires a large and rapid energy supply. In addition to the usual sugars and electrolytes contained in sports beverages, the patent includes and is expressly focused upon 0.5 to 2 grams of alpha-ketoglutaric acid. The patent specifically mentions glutamine, and it clearly states that glutamine is unstable and can only be used as a supplement in a few products. It is clear that the inventors of the patent felt glutamine would not work or be operative for the desired result. The patent focuses on alpha-ketoglutaric acid, another amino acid which is specifically different from glutamine as the desired additive.

U.S. Pat. No. 4,479,974 does discuss the use of glutamine in combination with other amino acids as a dry mix that can enhance the flavor and feel of a beverage. The dry mix they describe is purely for taste and not for the qualities needed in a sports beverage. Furthermore, the concentration of glutamine they describe, 0.2 grams in 1000 ml. (0.02%) is an order of magnitude below the glutamine compositions necessary and used herein.

It is an objective of the present invention to provide an oral replacement beverage formulation that enables one to have excellent water retention or absorption.

SUMMARY OF THE INVENTION

Applicant discloses a glutamine containing sports beverage which has unique breakthrough properties. Glutamine is a specific amino acid that provides enhanced absorption of fluid from the gastrointestinal track, improved immunity and resistance to infection, it maintains the integrity of the lining of the gastrointestinal track, it restores muscle mass, and it prevents overtraining syndrome. The glutamine containing beverage is stable and technologically easy to prepare. It is clearly contemplated to be the replacement and rehydration beverage of choice for endurance athletes.

DETAILED DESCRIPTION OF THE INVENTION

The present invention provides a beverage, namely an oral replacement solution that contains the specific amino acid glutamine. Glutamine is a neutral amino acid that is particularly useful for the present invention. Glutamine enhances sodium and water absorption like other amino acids, though it offers additional benefits as well. Glutamine is the most abundant amino acid in the human body and is the main constituent of muscle. In addition, glutamine has many unique metabolic functions. These functions include deamination in the kidneys and elimination of ammonium ions in the urine resulting in net excretion of hydrogen ions and maintenance of acid base homeostasis, it is also used as a nitrogen shuttle between different organs for various reactions and is used as an energy source for certain cells. In addition, rapidly dividing cells such as enterocytes, reticulocytes, and others use glutamine as an energy source. Intestinal mucosal integrity during critical illness is also dependent on glutamine. Nucleotides such as adenosine triphosphate (ATP), purines, pyrimidines and other amino acids utilize glutamine as a precursor in their synthesis.

Because the body can synthesize glutamine from other amino acids, it has not been considered an essential amino acid. However, under certain stress conditions such as starvation, acidosis, trauma, sepsis, and burns, increased glutamine efflux from muscle occurs and depletion may ensue.

Exercise places increased metabolic demands on muscle and other organ systems. Indeed, athletes have decrements in performance, prolonged periods of fatigue, depression and susceptibility to infections during prolonged exercise. This state has been called overtraining syndrome. There are similarities between overtraining syndrome in athletes and the chronic fatigue syndrome in the general population. Exhaustive exercise can impair immune function as well as lower plasma glutamine levels. Glutamine is incorporated into an oral replacement solution and provides several unique advantages when done so. These advantages include enhanced absorption of water and its sodium, and enhanced metabolism of ammonia, enhanced nucleotide synthesis, enhanced maintenance of intestinal mucosa and resistance to isohemia, improved immunity and prevention of overtraining syndrome.

It is an unique disclosure to use glutamine with other components as an oral replacement solution. Approximately 5 grams of L-glutamine raise serum levels and prevent infection. If an athlete ingests approximately 1 liter per hour of an oral rehydration solution containing 0.25% of glutamine, in two hours they would ingest approximately 5 grams. Thus, a 0.25% solution provides necessary concentration for oral replacement.

The invention focuses on the ingestion of one liter of a 6–8% maltodextrin solution over 2 hours to provide enough carbohydrates for an average athlete. The sodium concentration for rehydration (the higher the better) would be limited by palatability, but should be higher than 10–20 meq or 230–460 ml. of sodium per liter. For ingestion during exercise, amounts ranging from 10–20 meq would be acceptable. Lastly, the amount of glutamine should be about 5 grams per liter or approximately 0.5% of solution. The range of glutamine can be from greater than 0.0% up to, and including, 1.0 wt %.

Additional modifications and improvements of the present invention may also be apparent to those skilled in the art. Thus, the particular combination or position described and illustrated herein is intended to represent only one embodiment of the invention, and is not intended to be limiting and one must look to the entire spirit and scope of the invention.

What is claimed is:

1. An oral hydration enhancement replacement solution for endurance exercise and rehydration comprising water, sodium and glutamine.

2. The oral hydration enhancement replacement solution as claimed in claim 1, further comprising at least one carbohydrate.

3. The oral hydration enhancement replacement solution of claim 2, wherein the at least one carbohydrate is maltodextrin.

4. The oral hydration enhancement replacement solution of claim 1, wherein the glutamine is present in a range from greater than 0 wt % up to and including 1.0 wt %.

5. The oral hydration enhancement replacement solution of claim 1, wherein the glutamine is 0.50 wt %.

6. An aqueous oral hydration enhancement replacement solution beverage comprising 6–8 wt % maltodextrin, 10–20 meq sodium and 0.26–0.50 wt % glutamine.

7. A method for oral hydration for endurance exercise and rehydration comprising the steps of administering an aqueous formulation of glutamine over a period of time in an amount wherein up to 5 grams of glutamine are ingested.

* * * * *